United States Patent [19]

Armagnacq et al.

[11] Patent Number: 4,689,045

[45] Date of Patent: Aug. 25, 1987

[54] PROCEDURE FOR THE PREPARATION OF MODIFIED CELLULOSE

[75] Inventors: Sylviane Armagnacq, Cestas; Michel Bol, Taussat, both of France

[73] Assignee: La Cellulose du Pin, Bordeaux, France

[21] Appl. No.: 809,048

[22] Filed: Dec. 16, 1985

[30] Foreign Application Priority Data

Dec. 14, 1984 [FR] France ................ 84 19123

[51] Int. Cl.$^4$ ............................................. A61F 13/16
[52] U.S. Cl. .................................... 604/375; 8/120; 8/193; 8/DIG. 8; 428/913
[58] Field of Search .............. 8/DIG. 18, 120, 193; 428/913; 604/375

[56] References Cited

U.S. PATENT DOCUMENTS 4,036,588  7/1977  Williams ..................... 524/714
4,151,130  4/1979  Adams ........................ 525/54.3

Primary Examiner—James J. Bell
Attorney, Agent, or Firm—Oblon, Fisher, Spivak, McClelland & Maier

[57] ABSTRACT

A dry fibrous product made from modified cellulose, having improved properties of absorption and water and physiological liquid retention, as well as its production procedure. The cellulose contained in a cellulose paste is activated, acrylonitrile is grafted to the cellulose while its dry content is sufficient to obtain a grafting rate of about 200%; the grafted cellulose paste is hydrolyzed with an alkali; the product is washed with water until a state of maximum expansion is reached; the product is acidified to a pH which brings it to a state of minimum expansion after the water is removed; the product is converted to its salt form in the presence of a water-miscible liquid, and under an agitation which is sufficient to prevent the clustering of the fibers; this is effected so that the quantity of water, expressed by volume, does not exceed about 10% of the liquid phase; the product is dried.

18 Claims, 2 Drawing Figures

1

PROCEDURE FOR THE PREPARATION OF MODIFIED CELLULOSE

BACKGROUND OF THE INVENTION

1. Field of the Invention

This invention pertains to the preparation of cellulose derivative-based products having improved absorbent properties both with respect to water and physiological liquids, for example, blood or urine.

2. Background of the Prior Art

The market for disposable absorbent products, for example, diapers or surgical dressings, has grown rapidly in recent years. To meet the increasing and ever more exacting demand, the art has sought to develop products having a still higher absorbent capacity and smaller volume.

Currently conventional wood pastes have provided the majority of absorbent materials, due to their fibrous structure, whose absorption capacity and speed are known. These materials, such as, for example, fluff pastes, i.e., cellulose pastes, which are made from wood and bleached, then treated for sanitary use, have an absorption capacity of about 10 to 15 g of water per gram of paste.

But products having still better absorption capacities are sought.

For this purpose, it has already been proposed to combine a cellulose fibrous structure with hydrophilic polymers.

For example, the preparation is known for compound materials formed of alternating strata of cellulose fiber layers and layers of polymers, such as sodium polyacrylate, in powder form. Generally, a layer of powder between two cellulose layers is utilized. Such a structure presents improved properties of absorption and retention of water or physiological liquids, but the presence of the powder can be considered as a drawback in the handling of the product, especially in the area of hygiene.

An alternative approach is the preparation of cellulose derivatives made by the in situ grafting and polymerization of monomers on cellulose fibers of a paste derived from wood or another cellulose material, so as to produce a material possessing improved absorption and retention properties while being easier to handle.

Cellulose materials modified by polymers containing carboxyl groups or hydrolyzable functional groups are known in technology. An operation method of grafting a monomer at olefinic non-saturation, containing carboxyl groups (for example, an acrylic acid or salt) or functional hydrolyzable groups, for example, ethyl acrylate, butyl acrylate or acrylonitrile, and in situ polymerization, is described, for example, in patent U.S. Pat. No. 3 194 724. Moreover, French patent publication FR No. 2 276 423 describes an operatory mode for the preparation of a wood paste modified by grafting, notably polyacrylonitrile, and having water absorbent properties. According to the process which is described, the grafting itself is followed by a hydrolysis of the grafted fibers, a subsequent washing with water, which brings the product to its state of maximum expansion, an acidification to a pH bringing the product to its state of minimum expansion, the conversion of the product into its salt state, by adding soda in the presence of a water-methanol mixture, followed by a washing with pure alcohol to eliminate the residual soda, and drying. The cellulose material is then utilized in the form of sheets to form an absorbent product.

But the conditions indicated in document FR No. 2 276 423 present a certain number of inconveniences for the industrial production of materials having improved absorption and retention capacities for water or physiological liquids.

According to the applications given to the modified cellulose absorbent sheet which is obtained, it is appropriate that it possess or lack specific characteristics.

For example, one can envision the utilization of the sheet as it is, preserving its fibrous structure.

Or, one can envision the preparation of an absorbent product comprised of a mixture of a conventional fluff product and a certain amount of modified absorbent cellulose which has been defibrated so that it is more suitable for the mixture. In this application, the sheet must be easily defibrated, yielding cellulose fibers of an appropriate length so as not to decrease the product's absorbent properties.

This notion of aptitude for defibration of a fibrous product is particularly important to differentiate the comportment of cellulose pastes.

However, it has been noted that, if the cellulose sheets made through the use of the process described in French patent publication FR No. 2 276 423 present the appropriate water or physiological liquid absorption capacities, in sheet form, they nonetheless possess a hard and brittle aspect: this characteristic implies a poor aptitude for defibration which produces fibers which are too short after the defibration stage. Because of this shortness of the fibers, the capacity for absorption by capillary action is decreased, which, while bringing no modification to the capacity of absorption by expansion, decreases the total absorption capacity. Thus, the use of such a product is restricted to an applicaton in the form of a nondefibrated sheet.

SUMMARY OF THE INVENTION

The invention provides a modified cellulose-based fibrous products, which is obtained by grafting a hydrolyzable group to a cellulose material, which does not present these drawbacks.

More specifically, it provides dry cellulose fibrous products, having improved water or physiological fluid absorption and retention properties, compared to known materials, which maintain their fibrous structure while being suitable for defibration. These products can be processed in the form of continuous or discontinuous sheets, or in balls.

The fibrous products according to the invention have a water absorption capacity measured under a pressure of 25 mbars, which is greater than about 35 g per gram of product, and a capacity to absorb physiological liquid, represented by a 1% NaCl solution, measured under a pressure of 25 mbars, NaCl, which is greater than about 15 g per gram of product as well as an absorption speed, which can be measured at the same time as the absorption capacity, which is greater than about 15 g per minute and per gram of product for the saline solution. They also have a defibration aptitude which is at least five times, and preferably ten times that of the normally used products.

The invention also includes absorbent hygienic products containing the fibrous products described above.

The invention also encompasses to a process for the preparation of cellulose fibrous products according to the invention, by the grafting of a polymerizable monomer at olefinic non-saturation, having hydrolyzable functional groups, to a cellulose fibrous material, especially a cellulose paste, which constitutes a refinement of known processes.

According to the invention, a process is provided, which includes the following sequence of steps: the cellulose contained in the cellulose paste is activated, the polymerizable monomer at olefinic non-saturation having hydrolyzable functional groups is grafted to the cellulose, the grafted cellulose paste is hydrolyzed with an alkali, the product is washed with water until a maximum expansion state is reached, the product is acidified to a pH such that, after the water is removed, it is in its state of minimum expansion, the product is converted to its salt form, in the presence of a water-miscible liquid, and it is dried, with the initial dry content of the cellulose at the time of grafting being sufficient to produce a grafting rate of about 200%, the conversion of the product into its sail form being conducted under sufficient agitation to prevent the clustering of the fibers, and it is effected such that, immediately before the drying stage, the quantity of water does not exceed about 10% by volume of the liquid phase.

The combination of all of these conditions produces a product having a satisfactory aptitude for defibration.

According to a first variation of the procedure between the stage in which the product is converted into its salt form and the drying stage, so that the quantity of water expressed by volume does not exceed about 10% of the liquid phase before the drying stage, the reactive liquid is exchanged completely with a water-miscible liquid.

According to a second particularly advantageous variation of the process, the procedure as described above is modified in the following manner: the addition of the water-miscible liquid is replaced by a displacement by water-miscible liquid, of the acidified water which is present due to the acidification, followed by a dilution of the medium with said water-miscible liquid.

This variation presents the advantage of requiring a smaller amount of water-miscible liquid.

According to an advantageous characteristic of the invention, the transformation of the product into its salt form, in the presence of a water-miscible liquid, is performed by adding ammonia solution.

The use of ammonia solution presents the advantage, in the implementation of the process according to the invention, of avoiding an additional washing stage, to eliminate the excess amounts of the reactive. The ammonia solution can actually be directly eliminated during the drying process, because of its highly volatile nature, which is not the case with soda, which has already been proposed for use in this stage in the aforementioned patent.

Advantageously, the ammonia solution which is necessary in this stage issues from a prior stage in the process, which avoids any further addition of reactive. In fact, the hydrolysis of the grafted fibers and possibly of the homopolymer which is also formed, lead to the production of a great excess of ammonia solution, and the quantity which is released, placed in alcohol solution, is sufficient for the subsequent conversion of the fibrous product into its salt form.

The water-miscible liquid plays the role of a dispersant to prevent the clustering of the fibers. This can, for example, be an alcohol such as methanol, ethanol or isopropanol.

The initial cellulose material utilized can be wood paste, preferably bleached chemical paste, hydrolyzed wood, rayon or cotton paste.

DETAILED DESCRIPTION OF THE INVENTION

Figure 1:
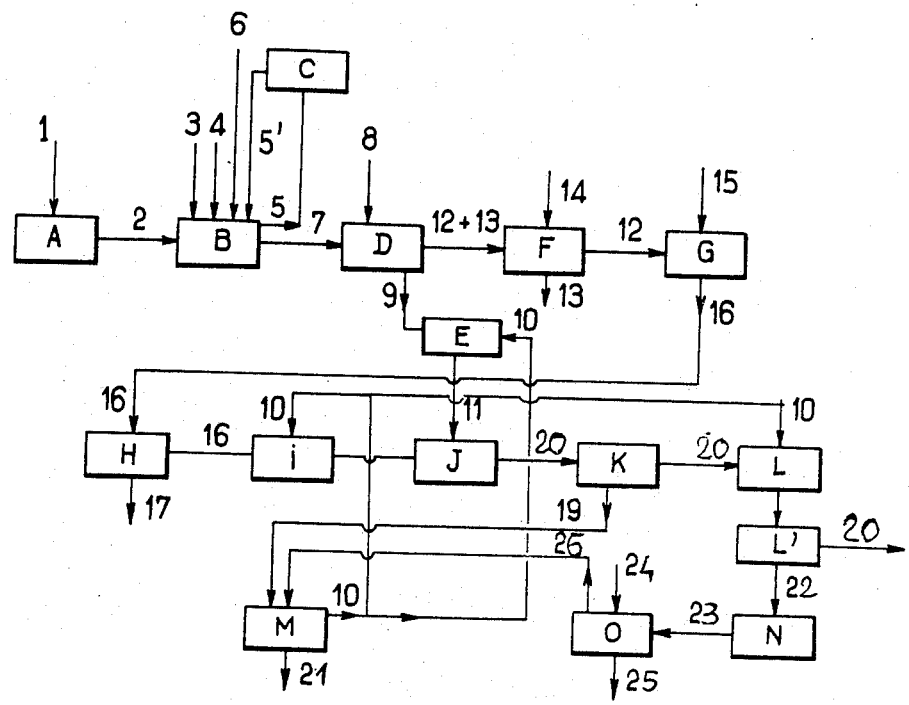
FIG. 1 is a schematic diagram of the process of the invention.

The polymerizable monomers at olefinic non-saturation having hydrolyzable functional groups can be any of the monomers known for their suitability for grafting on cellulose, and which present a better aptitude for grafting on cellulose than for homopolymer formation in the considered medium. They essentially include the vinyl and acrylic monomers and their derivatives, which are water insoluble or possess a very low degree of water solubility. For example, acrylonitrile, methacrylonitrile . . . and other monomers known to those of skill in the art may be used.

To obtain polymerizable monomer grafting rates of about 200%, which are desirable for the production of the products according to the invention, an initial dry content of the cellulose at the beginning of the grafting, before the introduction of the polymerizable monomer, of about a minimum of 20% is appropriate. With this condition achieved, along with an appropriate agitation of the fiber suspension during the conversion of the groups grafted to the cellulose fibers into their salt form, and with a water content not exceeding about 10% by volume of the liquid phase before drying, the final product can be easily defibrated when this procedure is deemed necessary or useful.

The grafting reaction can be conducted at a temperature which is in the neighborhood of the reflux temperature of the wateracrylonitrile azeotrope, i.e., at a temperature of about 70 degrees C.

Any grafting procedure can theoretically be utilized, through the use of chemical catalysts or radiation. However, it was found that a particular type of chemical catalyst presented both simple procedures for use and a moderate cost. According to this aspect of the invention, the cellulose is activated using an oxidizing agent which can be heat-decomposed and introduced into the cellulose material to be activated in a single stage. Such a catalyst is, for example, persulfate of ammonium, potassium or sodium. The utilization of such a polymerization catalyst presents the additional advantage of producing a white product, whose color does not change over time. Moreover, it was noted that the whiteness of the finished product could be improved by destroying the excess persulfate after the grafting is completed, through the use of a reducing agent, for example, sodium bisulfate. Thus, according to an additional characteristic of the invention, such a reducing agent is introduced after the grafting and before the hydrolysis.

The hydrolysis which follows the grafting can be done with NaOH, KOH, LiOH, and generally with any strong base. The base concentration is about 3% in NaOH equivalent to prevent a potential deterioration of the cellulose structure.

The hydrolysis temperatures can be between room temperature the boiling temperature of water, and the duration can vary from a few minutes to several days.

Thus, at 100 degrees C., the hydrolysis reaction lasts about one hour.

To dry the superabsorbent, while the grafted groups are in their salt form, with the quantity of water being limited to about 10% by volume, two different procedures can be utilized, depending on the desired form for the processing of the product. For processing on a spool, i.e., in the form of continuous sheets, the product is formed into sheets as soon as it has been converted into its salt form. The formation of sheets is followed by a drying operation on a paper-type machine, with the drying being accompanied by an evaporation of the water-miscible liquid contained in the reactive mixture and its collection. For production in balls, the product is concentrated immediately after its salt form is obtained, preferably to a dry content of about 15 to 25%, the product obtained is subsequently dried, using, for example, the "flash drying" technique.

In a preferred form, the following operative conditions are combined:

the cellulose catalyst is ammonium persulfate,
the dry content of the cellulose at the beginning of the grafting operation is 20%,
the grafted monomer is acrylonitrile,
the water wash is conducted until a dry content of 2.5% is reached,
the acidification of the product is conducted to a pH of 3, the acidified product is concentrated until a dry content of about 20 to 25% is reached,
the acidified water is displaced using ethanol,
the medium is diluted with ethanol.

Other characteristics and advantages of the invention will emerge during the following description of a detailed example of the embodiment of the invention.

EXAMPLES

Two examples of the embodiment of the invention, in which the grafted monomer is acrylonitrile, will be described below. The description will be given in reference to FIGS. 1 and 2, which show the sequence of the stages of the process.

The quantities mentioned lead to the production of one ton of "bone dry" (i.e., 100% dry) superabsorbent. The concentrations are expressed in dry content, with the dry content indicating the percentage by weight of the dry product compared to a raw product, when the raw product contains a volatile component.

The various stages of the process are indicated by letters.

Two comparative examples, which will demonstrate the improvements brought by the invention, will also be described.

Absorbent products can be characterized by a certain number of values which indicate their properties and thus also the improvements brought by the invention: these characteristics include the water retention value (VRE), the salt retention value (VRS), the absorption capacity and suitability for defibration. The methods utilized to establish these characteristics are given below:

1. VRE and VRS

The product is expanded in water or in saline solution; it is next centrifuged for one and one half minutes at 1250 g. The quantity of water or saline solution remaining in the product is determined by drying at 105 degrees C. to constant weight.

2. Water or physiological liquid absorption capacity

This is the essential quality for a paste for absorbent hygienic articles. It is expressed under two criteria: the absorption capacity and the absorption speed of the fibrous layer. A high absorption speed is very desirable for hygienic applications. The absorption capacity is obtained in the following manner: a small amount of the superabsorbent product is placed on a cylindrical component, the base of which is covered with a mechanical cloth. Weight is placed on the product so as to exert a constant pressure of 25 mbars. The cylindrical component is connected through the use of a flexible hose to a graduated burette containing the liquid, water or 1% NaCl saline solution. The cloth is in constant contact with the liquid. The burette is opened until the level stabilizes, which corresponds to the maximum absorption of liquid by the product.

The absorption speed is determined by measuring the quantity of liquid absorbed every 15 seconds.

3. Suitability of defibration

In the absence of a precise standard on this point, the applicant has defined a reliable method, determining the time which is required to obtain a complete individualization of the fibers contained in a sample.

To determine the suitability for defibration of a cellulose paste, the following procedure is utilized: the paste to be tested is maintained at 20 degrees C. for 24 hours, and is cut with a press-cutter into a lot of $2\times2$ cm squares. The equipment utilized for the measurement is a bowl with a hemispheric base, the type which is utilized in electric coffee grinders, equipped with a durable blade made of nonoxidizable steel, whose size and shape provide effective mixing and sweeping actions. The blade is screwed to a shaft which is equipped with ball bearings, endowed with a pulling cone which can be positioned on an 800 W motor base turning at 20,500 rotations per minute. A translucent cover prevents projections and allows the operations to be monitored.

For measurement, $3.0\pm0.05$ g of paste squares is weighed and placed on the bottom of the bowl. The bowl, which is closed and placed on the motor base, is activated in periods of ten seconds, alternating with a 5-second stop period to prevent excessive heating of the paste, until the fiber separation is judged sufficient. A sheet with the defibrated load is then pulled, on a laboratory bench, it is pressed and dried.

Examination of the sheet allows possible defibration defects to be detected, through the presence of grains or pellets. A new load is then defibrated for a slightly longer period of time, until a perfect consistency is obtained. The defiberability index corresponds to the total defibration time necessary to obtain this result. The longer the duration, the poorer the suitability of the paste for defibration.

COMPARATIVE EXAMPLE 1

A regular fluff paste for the production of absorbent cellulose articles is prepared.

Measurements of the properties of the absorbent product yielded the following results.

| | Defiberability index (seconds) | VRE (g/g of product) | VRS (g/g of product) | Capacity for absorption of saline solution (g/g of product) |
| --- | --- | --- | --- | --- |
| fluff | 25–50 | 1 | 1 | 10 |

COMPARATIVE EXAMPLE 2

An absorbent cellulose material is prepared according to the data in French patent publication No. 2 276 423.

A very poor defiberability index (greater than 50 seconds) is observed.

EXAMPLE ONE

Preparation of continuous sheets of superabsorbent by polyacrylonitrile grafting 0.34 air dry tons of bleached fluff-type chemical paste 1 is taken in A, where the paste is defibrated. The defibrated cellulose paste 2 is brought to B, in a reactor kept under agitation. At the same time as the defibrated cellulose paste, in B, 5 kg of ammonium persulfate 3 diluted in 0.9 m$^3$ of water and 730 kg of acrylonitrile monomer 4 are added, which are necessary for the grafting of the acrylonitrile polymer on the cellulose fibers, so that, at the beginning of the grafting, after the introduction of the acrylonitrile, the dry content is about 20%. Reactor B is brought in about 5 minutes to a temperature corresponding to the boiling temperature of the water-acrylonitrile azeotrope, or about 70 degrees C. The azeotrope 5, escapes and is condensed in C., then reintroduced in liquid form 5' in B. After about 45 minutes, the introduction of the liquid azeotrope into the reactor B is stopped to that it can be stored. The stored quantity will be subsequently introduced into B for the production of a new quantity of superabsorbent. After the excess acrylonitrile is eliminated, 8 m$^3$ of a solution 6 of sodium bisulfite at 0.38% dry material is added. It is allowed to react for 10 minutes. The grafted paste is introduced in a second reactor D for the hydrolysis operation. Simultaneously, 15 m$^3$ of a 45 g per liter alkaline NaOH solution 8 is introduced. The hydrolysis reaction occurs at 100 degrees C. for 30 minutes. During the reaction, the ammonia solution 9 escapes and is absorbed in E in a column by 95% ethanol 10. The water-alcohol-ammonia solution 11 which is produced is utilized subsequently in J for the neutralization of the acid form of the absorbent product 16. After the hydrolysis reaction, in F, a separation and washing of the absorbent fibrous phase 12 produced is conducted to eliminate the basic liquids and all of the non-grafted or dissolved molecules 13. For this washing, in F, the quantities of water necessary 14 to obtain the fibrous product in its maximum expansion phase 12 are introduced, corresponding to a dry content of about 2.5%, with the liquids 13 produced being eliminated. The fibrous product 12 is introduced in to vessel G for an acidification to pH3 leading to its conversion into acid form 16 to its minimum expansion state. Thus, 8 m$^3$ of water acidified with 35 g/l of H$_2$SO$_4$, 15 is introduced to G. The product obtained 16 is thickened to about a 20% dry content in vessel H, with the removal of the water and residues such as H$_2$SO$_4$ and Na$_2$SO$_4$ 17. To the product 16, about 6 m$^3$ of 95% ethanol 10 is added in at I.

The superabsorbent in acid form 16 in an alcohol medium is neutralized at J, where it is converted to its salt form, by adding the 95% ethanol and ammonia solution mixture 11 issuing from E. The neutralization occurs under agitation which is sufficient to prevent the clustering of the superabsorbent fibers.

The neutralized superabsorbent 18 is thickened in K to a dry content of about 20%. A complete exchange of the liquid in L is effected by 95% ethanol 10 such that the quantity of water in the product does not exceed about 10% by volume of the liquid phase. The material is next dried at L' using the flash drying technique. The alcohol which is collected 19 in case K is recycled to the distillation column in M. The distillation residue 21 which contains essentially water, traces of alcohol, Na$_2$SO$_4$, water-soluble (NH$_4$)$_2$SO$_4$ and traces of H$_2$SO$_4$ is removed. The vapor 22 produced by the drying in L' is condensed in case N. The liquid produced 23 is neutralized, O, by adding sulfuric acid 24, also causing the precipitation of (NH$_4$)$_2$SO$_4$ 25, which is removed from the circuit. The alcohol and residual water 26 are sent to M for the distilling operation.

Part of the alcohol 10 collected after the distillation operation in case M is recycled to the absorption column E. Another part is added to I and L as indicated above.

Thus, one ton of dry superabsorbent 20 is produced in fibrous form, which can be utilized for the production of hygienic products.

EXAMPLE 2

Figure 2:
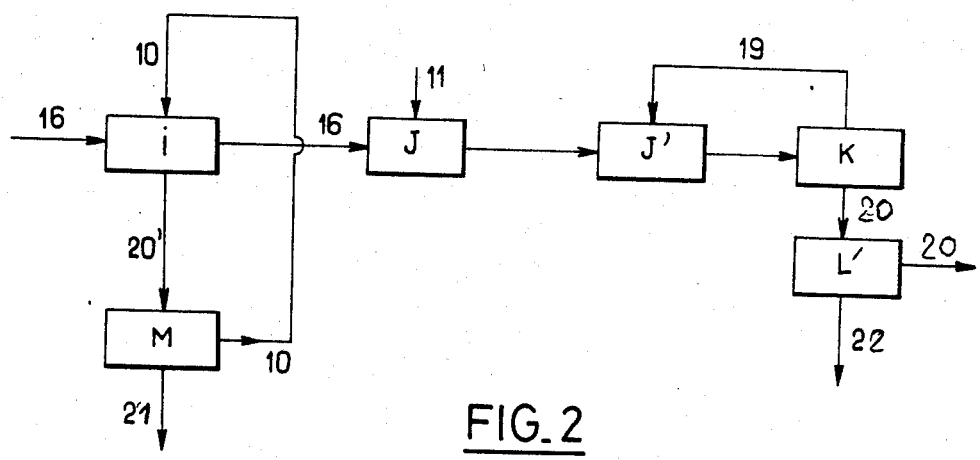
FIG. 2 is a schematic diagram of a modified process of the invention.

The procedure in example 1 is followed, with the modification of the process according to the sequence of stages indicated in FIG. 2. The modifications appear at the level of step I: instead of adding ethanol in case I, the acidified water is displaced by 6 m$^3$ of 95% ethanol 10. The superabsorbent in acid form 16 in an alcoholic medium is neutralized at J, in which it is converted to its salt form under agitation. The residue 20' from the ethanol wash in I is sent to the distillation column in case M. The superabsorbent is diluted is case J' in 95% ethanol 19 at 5 to 10 g per liter of the product.

It is made into sheets at K and dried L', with both operations being conducted in an appropriate paper machine. The liquid ethanol 19 collected at K is recycled to J' for the dilution operation. The ethanol vapor 22 from the drying in case L is condensed in case N (see diagram in FIG. 1).

The properties of the product obtained according to examples 1 and 2 are as follows:

| | VRE | VRS | Saline solution absorption capacity | Defiberability index | Acrylonitrile grafting index |
|---|---|---|---|---|---|
| Superabsorbent | 45 | 20 | 20 | 5 | 200% |

The saline solution absorption speed is 18 g per minute and per gram of product.

What is claimed as new and desired to be secured by Letters Patent of the United States is:

1. Dry modified cellulose-based fibrous product, comprising cellulose fibers to which a polymer in the form of an alkaline metal salt issuing from a polymerizable monomer at olefinic non-saturation, having hydrolyzable functional groups, is chemically grafted, characterized in that it has a water absorption capacity under a pressure of 25 mbars, which is greater than about 35 g per g of product, a 1% NaCl saline solution absorption capacity, under a pressure of 25 mbars, which is greater than about 15 g per g of product, a saline solution absorption speed which is greater than 15 g per minute and per g of product, and has a defiberability index, determined by the defibration time necessary to obtain a sheet without defibration defects from a past sample placed in a bowl equipped as an electric coffee grinder, which is under 20 seconds.

2. An absorbent hygienic product in the form of an absorbent layer for diapers, surgical dressings, sanitary material and the like, comprising a fibrous product according to claim 1.

3. Product of claim 1, wherein said defibrability index is under 10.

4. The product of claim 1 in the form of sheets.

5. The product of claim 1 in the form of balls.

6. Process for the preparation of a modified cellulose-based product according to claim 1, having water and physiological liquid retention capacities which are improved, comprising grafting a polymerizable monomer at olefinic non-saturation, having hydrolyzable functional groups, to a cellulose paste, thereby activating the cellulose contained in the cellulose paste, hydrolizing the grafted cellulose paste with an alkali, washing the product with water until a maximum expansion state is reached, acidifying the product to a pH bringing it to its state of minimum expansion after the water is eliminated, converting the product to its salt form in the presence of a water-miscible liquid and drying said product with the dry content of the cellulose during grafting being sufficient to obtain a grafting rate of about 200%, with the conversion of the product into its salt form being conducted under sufficient agitation to prevent the clustering of the fibers, and such that, immediately before the drying stage, the quantity of water does not exceed about 10% by volume of the liquid phase.

7. Process according to claim 6, wherein a complete exchange of the reactive liquid with a water-miscible liquid is effected, so that the quantity of water expressed by volume does not exceed about 10% before the drying stage.

8. Process according to claim 6, wherein the acidified water is displaced through the use of a water-miscible liquid, then the reactive medium is diluted with said watermiscible liquid, so that the quantity of water, expressed by volume, does not exceed about 10% of the liquid phase before the drying phase.

9. Process according to claim 6 wherein the polymerizable monomer is chosen from monomers suitable for grafting to cellulose and having a better aptitude for cellulose grafting than for the formation of homopolymers in the considered medium.

10. Process according to claim 9, characterized in that the polymerizable monomer is acrylonitrile.

11. Process according to claim 6 wherein the initial dry content of the cellulose at the beginning of the grafting, before the introduction of the polymerizable monomer, is at least 20%.

12. Process according to claim 6 wherein the cellulose is activated with a heat-decomposable oxidizing agent.

13. Process according to claim 12, wherein the oxidizing agent utilized is persulfate of sodium, ammonium or potassium.

14. Process according to claim 12 wherein the heat-decomposable oxidizing agent is eliminated after the grafting stage and before the hydrolysis stage.

15. Process according to claim 6 wherein the conversion of the product to its salt form is performed with ammonia solution.

16. Process according to claim 15, wherein the ammonia solution which is released during the hydrolysis of the grafted cellulose paste is collected and utilized to convert the product to its salt form, and is eliminated during drying.

17. Process according to claim 6 wherein the water-miscible liquid is an alcohol selected from the group consisting of methyl alcohol, ethyl alcohol, isopropyl alcohol and mixtures thereof.

18. Process for the preparation of a product according to claim 1 comprising activating a cellulose paste with ammonium persulfate, grafting acrylonitrile to the cellulose while the cellulose has a dry content of 20%, hydrolyzing the cellulose paste hydrolyzed with soda, washing the grafted and hydrolyzed fiber with water until a dry content of 2.5% is obtained, acidifying the washed fiber to a pH of 3, centrifuging the acidified product until a dry content of 20 to 25% is reached, displacing the acidified water through the us of ethanol, neutralizing the product by adding ammonia solution while agitating, adding ethanol to form a continuous sheet, the quantity of water not exceeding about 10% by volume of the liquid phase, and then drying the sheet.

* * * * *